(12) United States Patent
Li et al.

(10) Patent No.: US 10,828,830 B2
(45) Date of Patent: Nov. 10, 2020

(54) BIOPRINTER

(71) Applicant: REVOTEK CO., LTD, Chengdu, Sichuan (CN)

(72) Inventors: Yijun Li, Chengdu (CN); Deming Wang, Chengdu (CN); Leqing Zhang, Chengdu (CN); Xuemin Wen, Chengdu (CN)

(73) Assignee: Revotek Co., Ltd, Sichuan (CN)

( * ) Notice: Subject to any disclaimer, the term of this patent is extended or adjusted under 35 U.S.C. 154(b) by 189 days.

(21) Appl. No.: 16/067,479

(22) PCT Filed: Dec. 30, 2015

(86) PCT No.: PCT/CN2015/099827
§ 371 (c)(1),
(2) Date: Jun. 29, 2018

(87) PCT Pub. No.: WO2017/113171
PCT Pub. Date: Jul. 6, 2017

(65) Prior Publication Data
US 2019/0001568 A1 Jan. 3, 2019

(51) Int. Cl.
*B29C 64/209* (2017.01)
*B29C 64/259* (2017.01)
(Continued)

(52) U.S. Cl.
CPC .......... *B29C 64/209* (2017.08); *B33Y 30/00* (2014.12); *B41J 2/175* (2013.01); *B41J 2/17513* (2013.01);
(Continued)

(58) Field of Classification Search
CPC ... B29C 64/209; B29C 64/106; B29C 64/321; B29C 64/259; B41J 2/175; B41J 2/17553; B41J 2/17513
See application file for complete search history.

(56) References Cited

U.S. PATENT DOCUMENTS

| 7,399,175 B2 | 7/2008 | Arends et al. |
| 2015/0084238 A1 | 3/2015 | Bonassar et al. |
| 2017/0266876 A1* | 9/2017 | Hocker .................. B33Y 30/00 |

FOREIGN PATENT DOCUMENTS

| CA | 2943965 A1 | 10/2015 |
| CN | 203994731 | 12/2014 |

(Continued)

OTHER PUBLICATIONS

Extended European Search Report and Search Opinion for PCT/CN2015/099827, dated Jul. 23, 2019.

(Continued)

*Primary Examiner* — Joseph S Del Sole
*Assistant Examiner* — Mohamed K Ahmed Ali
(74) *Attorney, Agent, or Firm* — Wolf, Greenfield & Sack, P.C.

(57) ABSTRACT

The present disclosure relates to a bioprinter, which comprises a spray head, a connector and a bioprinting material container having a discharge pipe, wherein a first end of the connector is threadedly connected with the discharge pipe, and a second end of the connector is detachably connected with the spray head. The bioprinter is configured such that, a connector is provided between the discharge pipe of the bioprinting material container and the spray head, wherein the first end of the connector is threadedly connected with the discharge pipe, and the second end is detachably disposed on the spray head. Compared with the bilateral plugging manner in the prior art, it is only necessary to unscrew the bioprinting material container such as to realize rapid replacement, so that it is extremely convenient to add the biological printing material, thereby avoiding the problem that the connector is integrally pulled out and the temperature environment is damaged when the container replaced in the past, and presenting a high reliability.

10 Claims, 1 Drawing Sheet

(51) Int. Cl.
  *B29C 64/321* (2017.01)
  *B33Y 30/00* (2015.01)
  *C12M 3/00* (2006.01)
  *B41J 2/175* (2006.01)
  *C12M 1/26* (2006.01)
  *B29C 64/106* (2017.01)

(52) U.S. Cl.
  CPC ............ *B41J 2/17553* (2013.01); *C12M 3/00* (2013.01); *C12M 21/08* (2013.01); *B29C 64/106* (2017.08); *B29C 64/259* (2017.08); *B29C 64/321* (2017.08); *C12M 33/00* (2013.01)

(56) References Cited

FOREIGN PATENT DOCUMENTS

| CN | 204076844 | | 1/2015 |
|---|---|---|---|
| CN | 104369380 | | 2/2015 |
| CN | 104786495 | A | 7/2015 |
| CN | 204640815 | | 9/2015 |
| CN | 105167879 | A | 12/2015 |
| CN | 105647802 | A | 6/2016 |
| CN | 205291606 | U * | 6/2016 |
| CN | 205443253 | U | 8/2016 |
| JP | 9-109203 | | 4/1997 |
| JP | 2013-237227 | A | 11/2013 |
| WO | WO 2011/125475 | A1 | 10/2011 |
| WO | WO 2015/196085 | A2 | 12/2015 |

OTHER PUBLICATIONS

Japanese Office Action dated Dec. 3, 2019 in connection with Japanese Patent Application No. 2018-534171.
JP2018-534171, Dec. 3, 2019, Japanese Office Action.
International Search Report and Written Opinon for PCT/CN2015/099827, dated Sep. 20, 2016.
International Preliminary Report on Patentability for PCT/CN2015/099827, dated Jul. 3, 2018.

* cited by examiner

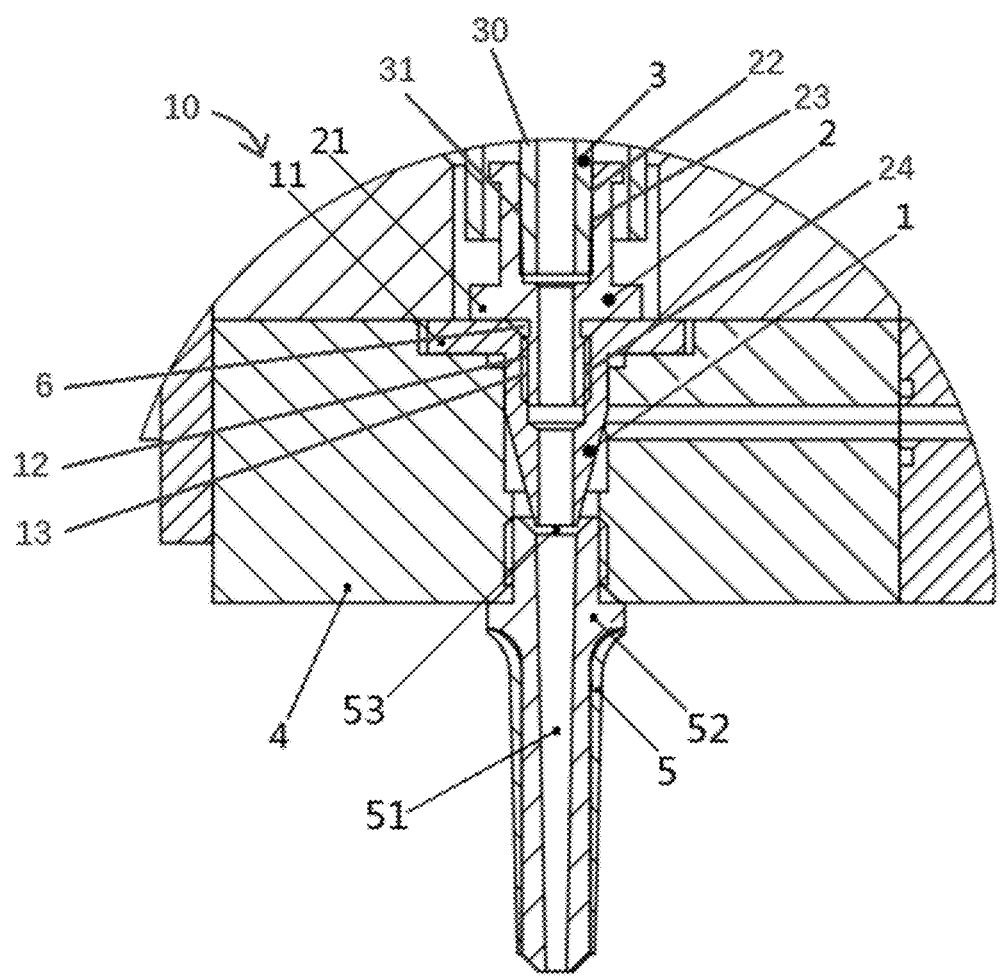

BIOPRINTER

RELATED APPLICATIONS

This application is a national stage filing under 35 U.S.C. § 371 of International Patent Application Serial No. PCT/CN2015/099827, filed Dec. 30, 2015, the content of which is incorporated herein by reference in its entirety.

TECHNICAL FIELD

The present disclosure relates to the field of bioprinting, and especially relates to a bioprinter.

BACKGROUND ART 3D bioprinting refers to the printing of biological materials (including natural biological materials and synthetic biological materials or cellular solutions) into a designed three-dimensional structure through the principles and methods of 3D printing. Differing from those printed by ordinary 3D printing technology, the biological tissues or organs produced by 3D bioprinting technology have certain biological functions and need to provide conditions for the further growth of cells and tissues. Exactly due to the aforementioned characteristics, the 3D bioprinting technology is confronted with many specific technical problems in development.

In the field of 3D bioprinting, the print technique of taking cells as a printing material is referred to as cell three-dimensional printing technology. People may utilize cells and biocompatible materials to make bio-ink. The spray head moves and sprays the bio-ink, and the movement of the spray head is controlled by a program to the print bio-ink. The bio-ink is printed and molded according to a three-dimensionally constructed digital model of a preset target print object.

The disadvantages of the prior art lie in that:

The existing bioprinter generally uses a quick-insertion structure to connect the spray head and the printing material container, such that both ends of the quick-insertion structure are respectively closely plugged and socketed to the spray head and the printing material container. Such connection structure has a poor stability. The quick-insertion structure usually also needs to cooperate with other tubes in use, which is unfavorable for temperature control of the printing material, and moreover, there is a need for a large operation space during the installation and removal.

CONTENT OF THE DISCLOSURE

In order to overcome the above technical defects, the technical problem solved by the present disclosure is to provide a bioprinter, which is capable of realizing rapid replacement of a bioprinting material container, and presents a favorable connection stability and thermal insulation property.

In order to solve the aforementioned technical problem, the present disclosure provides a bioprinter, which comprises a spray head, a connector and a bioprinting material container having a discharge pipe, wherein a first end of the connector is threadedly connected with the discharge pipe, and a second end of the connector is detachably connected with the spray head.

Further, an outlet end of the discharge pipe is provided with a first external thread, and the first end of the connector is provided with a first accommodating cavity for accommodating the outlet end, wherein the first accommodating cavity is internally provided with a first internal thread mated with the first external thread, and the outlet end is inserted and threadedly connected into the first end of the connector.

Further, the first accommodating cavity has a tapered section taken along a direction towards the second end of the connector.

Further, the section of the first accommodating cavity is in a conical shape.

Further, the conical shape has a conical degree of 6%.

Further, there further comprises a mounting block, on which the spray head is detachably and non-rotatably mounted.

Further, a circumferential limit structure is provided between the spray head and the mounting block, to limit a relative rotation between the spray head and the mounting block.

Further, a detachable circumferential limit member is provided between the connector and the spray head, to limit a relative rotation between the connector and the spray head.

Further, there further comprises a mounting block on which the spray head is detachably and non-rotatably mounted, wherein the second end of the connector is provided with a second external thread, the spray head is provided with a second accommodating cavity for accommodating the second end of the connector, the second accommodating cavity is internally provided with a second internal thread mated with the second external thread, and the second end of the connector is inserted and threadedly connected into the second accommodating cavity.

Further, the connector comprises an axial limit portion provided between the first end and the second end of the connector and projecting radially, and the bioprinter comprises a resilient washer provided between the spray head and the axial limit portion.

Further, a threaded fastening force between the second end of the connector and the spray head is greater than that between the first end of the connector and the discharge pipe.

Further, the bottom of the spray head includes an extension rod, which is spaced apart and disposed adjacent to an outlet of the spray head, wherein the extension rod is internally provided with an elongated flow channel for allowing that a fluid printing unit serving as a biological printing material is guided by the flow channel such as to be orientedly sprayed.

Further, an open recess is provided on an end surface of the extension rod adjacent to the spray head. An outlet of the open recess communicates with the flow channel, and the spray head extends into the open recess. The open recess is tapered toward the flow channel, and an second material flow channel is formed between an outer wall of the spray head and the open recess, forming a cavity between the outlet of the spray head and the outlet of the open recess. The second material fluid passing through the second material flow channel wraps a first material fluid sprayed from the outlet of the spray head in the chamber, so as to form a fluid printing unit.

Further, the flow channel is tapered from its inlet to outlet.

Further, the flow channel has a conical section taken along a flow direction of the fluid printing unit.

Further, the bioprinter is a 3D bioprinter.

Accordingly, on the basis of the aforementioned technical solution, the present disclosure provides a bioprinter, which is configured such that, a connector is provided between the spray head and the discharge pipe of the bioprinting material container, wherein the first end of the connector is threadedly connected with the discharge pipe, and the second end is detachably disposed on the spray head. Compared with the bilateral plugging manner in the prior art, the present technical solution only needs to unscrew the bioprinting material container such as to realize rapid replacement, so that it is extremely convenient to add the biological printing material, thereby avoiding the problem that the connector is integrally pulled out and the ambient temperature is damaged when the container replaced in the past, and presenting a high reliability.

BRIEF DESCRIPTION OF THE DRAWINGS

The drawings described herein are used to provide a further understanding of the present disclosure and constitute a part of the present application. The illustrative embodiments of the present disclosure as well as the descriptions thereof, which are merely used for explaining the present disclosure, do not constitute improper definitions on the present disclosure. In the drawings:

FIG. 1 is a schematic view of the structure according to one embodiment of the bioprinter of the present disclosure.

EMBODIMENTS

Next, the technical solution of the present disclosure is further described in detail by means of the drawings and embodiments.

The specific embodiments of the present disclosure are further described in order to facilitate understanding of the concept of the present disclosure, the technical problem to be solved, the technical features constituting the technical solution and the technical effect produced therefrom. It is necessary to explain that, the explanations for such embodiments do not constitute definitions on the present disclosure. In addition, the technical features involved in the embodiments of the present disclosure described below may be combined with each other as long as they do not constitute a conflict therebetween.

Considering that the existing bioprinter generally uses a quick-insertion structure to connect the spray head and the printing material container, such that both ends of the quick-insertion structure are respectively plugged and socketed to the spray head and the printing material container, such connection structure has a poor stability. The quick-insertion structure usually also needs to cooperate with other tubes in use, which is unfavorable for temperature control of the printing material, and moreover, there is a need for a large operation space during the installation and removal.

The present disclosure designs a bioprinter, which is configured such that, a connector is provided between the spray head and the discharge pipe of the bioprinting material container, wherein the first end of the connector is threadedly connected with the discharge pipe, and the second end is detachably disposed on the spray head. Compared with the bilateral plugging manner in the prior art, the present technical solution only needs to unscrew the bioprinting material container such as to realize rapid replacement, so that it is extremely convenient to add the biological printing material, thereby avoiding the problem that the connector is integrally pulled out and the ambient temperature of the spray head is damaged when the container replaced in the past, and presenting a high reliability.

In one illustrative embodiment of the bioprinter of the present disclosure, as shown in FIG. 1, the bioprinter comprises a spray head 1, a connector 2 and a bioprinting material container 30 having a discharge pipe 3, wherein a first end of the connector 2 is threadedly connected with the discharge pipe 3, and a second end of the connector 2 is detachably connected with the spray head 1.

In the illustrative embodiment, a connector 2 is provided between the spray head 1 and the discharge pipe 3 of the bioprinting material container (not shown in the FIGURE), wherein the first end of the connector 2 is threadedly connected with the discharge pipe 3, and the second end is detachably disposed on the spray head 1. Compared with the bilateral plugging manner in the prior art, in the present embodiment, for example, by controlling the temperatures of the main material container and the auxiliary material container, when the temperature reaches a set temperature, a biological material is respectively added into the corresponding container; a corresponding connector is inserted into the discharge pipe 3 of the corresponding container, and rotated clockwise. In this way, it is only necessary to rotate the bioprinting material container. Correspondingly, the discharge pipe 3 rotates relative to the connector, and the bioprinting material container is unscrewed such as to realize rapid replacement, so that it is extremely convenient to add the biological printing material (for example bio-ink), thereby avoiding the problem that the bilaterally plugged connector is integrally pulled out to damage the ambient temperature of the spray head when the bioprinting material container is replaced in the past, and avoiding the problem that the operation space is limited so that it is difficult to operate when the bilaterally plugged connector is integrally pulled out.

As one preferred embodiment in which the connector 2 is threadedly connected with the discharge pipe 3, as shown in FIG. 1, an outlet end of the discharge pipe 3 is provided with a first external thread 31, and the first end of the connector 2 is provided with a first accommodating cavity 22 for accommodating the outlet end, wherein the first accommodating cavity is internally provided with a first internal thread 23 mated with the first external thread, and the outlet end is inserted and threadedly connected into the first end of the connector 2. Since the bioprinting material container needs to be replaced frequently, by providing an external thread structure at the outlet end of the discharge pipe 3, the discharge pipe 3 is helically screwed into the first accommodating cavity of the connector 2. Compared to the internal thread structure provided such that the connector is screwed into the discharge pipe 3, the preferred embodiment facilitates aligning the positioning the discharge pipe 3, so that it is more convenient and quick to install the bioprinting material container.

Certainly, by providing the internal thread structure at the outlet end of the discharge pipe 3, it also pertains to the protection scope of the present disclosure that the first end of the connector 2 is helically screwed into the outlet end of the discharge pipe 3.

As an improvement to the aforementioned embodiment, as shown in FIG. 1, the first accommodating cavity is tapered along a direction toward the second end of the connector 2. The inner wall of the first accommodating cavity of the connector 2 is provided with a thread mating surface that is tapered toward the second end of the connector. That is, a first accommodating cavity tapered towards the spray head 1 is provided. After the outlet end of the discharge pipe 3 is inserted into the first accommodating cavity, the side of the discharge pipe 3 is tightly fitted with the connector 2 by a tapered fit surface, so that there are a more tight and firm connection and a favorable sealing property.

Preferably, the first accommodating cavity has a conical section. The first accommodating cavity in a conical shape which presents a symmetrical structure, can ensure that the first end of the connector 2 uniformly seals and wraps the outlet end of the discharge pipe 3 circumferentially, so as to further obtain a better sealing effect. Moreover, the first accommodating cavity in a conical shape is easy to process, and facilitates the unscrewing of the discharge pipe 3. Preferably, the section of the first accommodating cavity has a conical degree of 6%, that is, the first accommodating cavity uses a design having a conical degree of 6% (Luer). Within the preferred value range, the pressure resistance of 500 KPa at the connection portion is ensured, and the leakage of the biological printing material is effectively avoided.

As one preferred embodiment of the bioprinter of the present disclosure, as shown in FIG. 1, the bioprinter further comprises a mounting block 4, on which the spray head 1 is detachably and non-rotatably mounted. The mounting block 4 is used for mounting and positioning the spray head 1. By detachably mounting the spray head 1 on the mounting block 4, it is possible to facilitate replacing the spray head 1 of different specifications. The spray head 1 is detachably and non-rotatably mounted on the mounting block 4. A detachable circumferential limit member is provided between the connector 2 and the spray head 1, such that the connector 2 cannot rotate relative to the spray head 1. In this way, it is possible to avoid a follow-up of the spray head 1 and the connector 2 relative to the mounting block 4 when the discharge pipe 3 rotates.

Specifically, it may be realized that the spray head 1 is non-rotatable relative to the mounting block 4 by providing a circumferential limit structure 10 between the spray head 1 and the mounting block 4. For example, it is possible to process the outlet end of the spray head 1 into a cylinder having a cross section in a non-circular shape, and insert the same into a corresponding mounting passage having a cross section in a non-circular shape in the mounting block 4. As shown in FIG. 1, one end of the spray head 1 may be provided with a radial protrusion 11 for cooperating with the recess of the mounting block 4.

As another specific embodiment of the bioprinter of the present disclosure, as shown in FIG. 1, the bioprinter further comprises a mounting block 4 on which the spray head 1 is detachably and non-rotatably mounted, wherein the second end of the connector 2 is provided with a second external thread 24, the spray head 1 is provided with a second accommodating cavity 12 for accommodating the second end of the connector 2, the second accommodating cavity is internally provided with a second internal thread 13 mated with the second external thread 24, and the second end of the connector 2 is inserted and threadedly connected into the second accommodating cavity. By providing a second external thread on the second end of the connector 2, the second end of the connector 2 is helically screwed into the second accommodating cavity of the spray head 1, so that the connector 2 is fastenedly connected to the spray head 1, avoiding leakage of the biological printing material at the connection. Preferably, as shown in FIG. 1, the connector 2 further includes an axial limit portion 21 provided between the first end and the second end of the connector 2 and projecting radially, and the bioprinter further comprises a resilient washer (not shown in the FIGURE) provided between the spray head 1 and the axial limit portion 21. The axial limit portion 21 enables the connector 2 to obtain a better axial positioning, while the resilient washer disposed between the spray head 1 and the axial limit portion 21 can ensure that the threaded connection between the connector 2 and the spray head 1 has a greater pre-tightening force, avoiding follow-up of the connector 2 relative to the spray head 1 when the discharge pipe 3 rotates.

In addition, the threaded fastening force between the connector 2 and the spray head 1 is greater than that between the connector 2 and the discharge pipe 3, so that when the discharge pipe 3 and the connector 2 are disconnected by rotating the bioprinting material container, even in the case where the connector 2 and the spray head 1 are not provided with a circumferential positioning member, the connector 2 and the spray head 1 may not rotate together along with the bioprinting material container as well.

According to another aspect of the present disclosure, considering that the existing bioprinter directly sprays the cells to a printing platform at the spray head, and a fluid as a printing material may be subjected to the damage caused by the mechanical force in the printing process, the spray head located on an X-axis motion platform in the present disclosure is configured such that a fluid print unit serving as a biological printing material is orientedly sprayed through the flow channel by providing an extension rod having an elongated flow channel adjacent to the outlet of the spray head. The flow channel can protect the fluid printing unit and reduce the damage of the fluid printing unit by the mechanical force in the printing process, so that it presents a high reliability.

In the illustrative embodiment, the extension rod 5 having a flow channel 51 may be disposed at a position adjacent to the outlet of the spray head 1 by means of a mounting block 4, and the fluid printing unit serving as a biological printing material is guided by the flow channel 51 such as to be orientedly sprayed. Compared to the structure in the prior art where the bottom outlet is suddenly narrowed, the fluid printing unit is subjected to a more uniform pressure in the draining and spraying process, and easily maintains a favorable flow ability. The flow direction of the biological printing material is more stable, which relieves the condition of mutual crowd and compression between the cells, and reduces the damage of the fluid printing unit by the mechanical force in the printing process.

The fluid printing unit refers to a minimum printing unit of a biological printing material, which may be a minimum unit composed of a single main material fluid (for example bio-ink), and may also be a minimum unit of mixed fluids consisting of a main material fluid wrapped with an auxiliary material fluid (for example hydrogel).

The flow channel 51 can perform an oriented sequence of the fluid printing unit, so as to reduce the possibility of clogging. For a fluid printing unit which is a mixed fluid printing unit formed by wrapping the main material fluid with the auxiliary material fluid, the flow channel 51 also facilitates the auxiliary material fluid to uniformly wrap and protect the main material fluid.

In addition, since the flow channel 51 which presents an elongated shape prevents the damage produced by the friction between the biological printing material and the metal material in the printing process, the flow channel 51 can protect the fluid printing unit and reduce the influence of the damage of the fluid printing unit by the mechanical force in the printing process.

The flow channel 51 may be straight as shown in FIG. 1 so that the fluid printing unit is sprayed downwards, and may also be arranged in a curved structural form according to the printing requirements, so as to provide more options in the spray direction.

As shown in FIG. 1, a thermal insulation member 52 may also be provided on the outer periphery of the extension rod 5. The thermal insulation member 52 can ensure that the fluid printing unit keeps a desired temperature in the flow channel 51 and maintains the activity of the fluid printing unit. Furthermore, such structural form overcomes the technical drawback that the spray head has to project certain length so as to facilitate applying a sprayed material in the case without an extension rod while thermal insulation is not available.

As an improvement to one aspect of the aforementioned embodiment, as shown in FIG. 1, the flow channel 51 is tapered from its inlet to outlet. The flow channel 51 is designed such that the fluid printing unit travels in the flow channel 51 to facilitate raising the flow rate of the fluid printing unit at the outlet of the flow channel 51 and reduce the possibility of its clogging. Preferably, the cross section of the flow channel 51 taken along the flow direction of the fluid printing unit is conical. The conical flow channel 51 in a structural form similar to a funnel or a subway gate makes a more uniform distribution of the fluid printing unit in the flow channel 51, and further reduces the possibility of its clogging. Moreover, the conical flow channel which is easy to process, presents a favorable implementability.

Preferably, on the one hand, the inlet of the flow channel 51 is sized to be n times the size of the fluid printing unit, wherein n=2-5. Within the preferable size range, the problem of clogging at the inlet of the flow channel 51 can be effectively avoided. Preferably, the inlet of the flow channel 51 is sized to be twice the size of the fluid printing unit so that the inlet of the flow channel 51 is only accessible for two fluid printing units side by side at most. Since the flow channel 51 is a tapered flow channel, it is only possible to flow out a single row of fluid printing units reaching the outlet of the flow channel 51, such as to enable further reducing the possibility of the clogging of the fluid printing unit, and facilitating the spray of the fluid printing units in a single row.

On the other hand, the outlet of the flow channel 51 is sized to be 1-1.5 times, preferably 1.2 times the size of the fluid printing unit. Within the size range, the flow passage 51 not only facilitates the spray of the fluid printing units in a single row, but also can avoid that the auxiliary material fluid wraps the main material fluid in an excessive thickness in the case of ensuring that the main material fluid is not damaged, and facilitate further raising the flow rate of the fluid printing unit at the outlet of the flow channel, and ensure the continuity and uniformity of the spray of the fluid printing unit in a single row.

As an improvement to another aspect of the aforementioned embodiment, as shown in FIG. 1, an open recess 53 is provided on an end surface of the extension rod 5 adjacent to the spray head 1. An outlet of the open recess 53 communicates with the flow channel 51, and the spray head 1 extends into the open recess 53. The cross section of the open recess 53 is tapered toward the flow channel 51, and an auxiliary material flow channel is formed between an outer wall of the spray head 1 and the open recess 53, forming a cavity between the outlet of the spray head 1 and the outlet of the open recess 53. The auxiliary material fluid passing through the auxiliary material flow channel wraps a main material fluid sprayed from the outlet of the spray head 1 in the chamber, so as to form a fluid printing unit. By providing a tapered open recess 53 on an end face of the extension rod 5 adjacent to the spray head 1, an auxiliary material flow channel is formed between an outer wall of the spray head 1 and the open recess 53, forming a cavity between the outlet of the spray head 1 and the outlet of the open recess 53. The auxiliary material fluid (for example hydrogel) enters the chamber through the auxiliary flow channel and wraps the main material fluid (for example bio-ink) sprayed from the spray head, so as to form a mixed fluid printing unit. Among them, the main material fluid may be a homogeneous, non-homogeneous (e.g., granular mixture), continuous or discontinuous fluid.

Specifically, since an auxiliary material flow channel is formed between the outer wall of the spray head 1 and the tapered open recess 53, the auxiliary material flow channel has the function of a uniform pressure. Even if the auxiliary material enters the auxiliary material flow channel from one side as shown in FIG. 1, it still presents a uniform pressure intensity within the auxiliary material flow channel, thereby ensuring that the biological material presents a uniform wrapping effect at one side adjacent to or far from the auxiliary material inlet. In the embodiment, the section of the open recess 53 taken along the flow direction of the fluid printing unit, is preferably conical, and the open recess 53 presenting a conical structure allows the auxiliary material fluid to flow along a conical face of the open recess 53, which produces the effect of converging towards the outlet of the spray head 1, and facilitates the uniform wrapping of the main material fluid unit by the auxiliary material fluid unit. The open recess 53 of the structural form can also ensure a more stable flow direction within the chamber.

The mixed fluid printing unit flows within the open recess 53, and the open recess 53 facilitates the convergence of the fluid printing unit toward the flow channel 51 of the extension rod 5, so as to ensure that the flow direction of the mixed fluid printing unit within the chamber is more stable, and avoid its diffusion in the auxiliary material flow channel.

As shown in FIG. 1, there is a gap between the outlet of the spray head 1 and the open recess 53. Preferably, the gap between the outlet of the spray head 1 and the open recess 53 is smaller than the size of the fluid printing unit, which can prevent the fluid printing unit from reversely flowing toward the auxiliary material flow channel, and ensure that the fluid printing unit within the chamber flows stably to the flow channel 51.

In one embodiment of the bioprinter spray head assembly according to the present disclosure, the process of wrapping the main material fluid with the auxiliary material flow is as follows:

The main material fluid after being sprayed from the spray head 1, enters the chamber between the outlet of the spray head 1 and the outlet of the open recess 53. The auxiliary material fluid enters the chamber through the auxiliary material flow channel formed between the outer wall of the spray head 1 and the open recess 53. The auxiliary material fluid in the chamber has certain pressure, and the auxiliary material fluid is compressed such as to be adhered to a portion of the main material fluid unit projecting from the spray head 1. Until the entire main material fluid unit is sprayed, the auxiliary material fluid completely wraps the main material fluid unit, to form a mixed fluid printing unit. At this time, a portion of the fluid printing unit has already entered the flow channel 51 of the extension rod 5. Finally, the main material fluid unit enters the flow channel 51 of the extension rod 5 under the continuous wrapping of the auxiliary material fluid, and the main material fluid unit surrounded by the auxiliary material fluid orientedly flows within the flow channel 51, and is uniformly wrapped, and sequentially sprayed.

In the flow process, the main material fluid is adequately and uniformly wrapped by the auxiliary material fluid, so that the structure also allows the auxiliary material is uniformly and adequately wrapped. The auxiliary material fluid which is wrapped around the main material to form a protective structure before the main material fluid is sprayed from the outlet of the flow channel 51, further reduces the influence of the printing process over the main material fluid.

The above-combined embodiments make detailed explanations for the embodiments of the present disclosure, but the present disclosure is not limited to the embodiments described. For example, it may also be realized that the spray head 1 is detachably and non-rotatably mounted on the mounting block 4 by an interference fit between the spray head 1 and the mounting block 4. For a person skilled in the art, multiple changes, modifications, equivalent replacements, and variations made to such embodiments still fall within the protection scope of the present disclosure without departing from the principles and substantive spirit of the present disclosure.

What is claimed is:

1. A bioprinter, comprising a spray head, a connector and a bioprinting material container having a discharge pipe, wherein a first end of the connector is threadedly connected with the discharge pipe, and a second end of the connector is detachably connected with the spray head, a detachable circumferential limit member is provided between the connector and the spray head, the circumferential limit member is configured to limit a relative rotation between the connector and the spray head; and a mounting block on which the spray head is detachably and non-rotatably mounted, wherein the second end of the connector is provided with a second external thread, the spray head is provided with a second accommodating cavity for accommodating the second end of the connector, the second accommodating cavity is internally provided with a second internal thread mated with the second external thread, and the second end of the connector is inserted and threadedly connected into the second accommodating cavity.

2. The bioprinter according to claim 1, wherein an outlet end of the discharge pipe is provided with a first external thread, and the first end of the connector is provided with a first accommodating cavity for accommodating the outlet end, wherein the first accommodating cavity is internally provided with a first internal thread mated with the first external thread, and the outlet end is inserted and threadedly connected into the first end of the connector.

3. The bioprinter according to claim 2, wherein the first accommodating cavity has a tapered section taken along a direction towards the second end of the connector.

4. The bioprinter according to claim 3, wherein the section of the first accommodating cavity is in a conical shape.

5. The bioprinter according to claim 4, wherein the conical shape has a conical degree of 6%.

6. The bioprinter according to claim 1, further comprising a mounting block on which the spray head is detachably and non-rotatably mounted.

7. The bioprinter according to claim 6, wherein a circumferential limiter is provided between the spray head and the mounting block, wherein the circumferential limiter is configured to limit a relative rotation between the spray head and the mounting block.

8. The bioprinter according to claim 1, wherein the connector comprises an axial limit portion provided between the first end and the second end of the connector and projecting radially, and the bioprinter comprises a resilient washer provided between the spray head and the axial limit portion.

9. The bioprinter according to claim 1, wherein a threaded fastening force between the second end of the connector and the spray head is greater than that between the first end of the connector and the discharge pipe.

10. The bioprinter according to claim 1, wherein the bioprinter is a 3D bioprinter.

* * * * *